(12) United States Patent
Tschuncky et al.

(10) Patent No.: US 7,645,367 B2
(45) Date of Patent: Jan. 12, 2010

(54) GAS-MEASURING SYSTEM WITH GAS SENSOR AND GAS GENERATOR

(75) Inventors: Peter Tschuncky, Lübeck (DE); Herbert Kiesele, Lübeck (DE); Uwe Kühn, Wesenberg (DE); Frank Mett, Lübeck (DE); Andreas Hengstenberg, Reinfeld (DE); Kerstin Caro, Timmendorfer Strand (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 669 days.

(21) Appl. No.: 11/348,748

(22) Filed: Feb. 7, 2006

(65) Prior Publication Data
US 2006/0230813 A1    Oct. 19, 2006

(30) Foreign Application Priority Data
Apr. 15, 2005    (DE) ................ 10 2005 017 445

(51) Int. Cl.
*G01N 27/26* (2006.01)
*G01N 27/404* (2006.01)
(52) U.S. Cl. ................ 204/401; 73/23.2; 204/412; 204/415; 204/426
(58) Field of Classification Search ........ 204/401, 204/412; 73/23.2
See application file for complete search history.

(56) References Cited

U.S. PATENT DOCUMENTS

| | | | |
|---|---|---|---|
| 4,151,739 A | 5/1979 | Breuer et al. | |
| 6,200,443 B1 * | 3/2001 | Shen et al. | 204/401 |
| 6,454,923 B1 | 9/2002 | Dodgson et al. | |
| 6,558,519 B1 * | 5/2003 | Dodgson et al. | 204/401 |
| 6,632,674 B1 * | 10/2003 | Warburton | 436/8 |
| 6,635,160 B1 * | 10/2003 | Dodgson | 204/401 |
| 2003/0145644 A1 * | 8/2003 | Rabbett et al. | 73/1.06 |

FOREIGN PATENT DOCUMENTS

| | | |
|---|---|---|
| DE | 44 25 889 A1 | 3/1996 |
| EP | 0 744 620 | 11/1996 |
| EP | 0 890 837 A2 | 1/1999 |
| EP | 1 492 070 A2 | 12/2004 |
| GB | 2 254 696 | 10/1992 |
| GB | 2 291 189 | 1/1996 |
| WO | WO 98/25139 | 6/1998 |
| WO | WO 03/067253 | 8/2003 |

* cited by examiner

*Primary Examiner*—Harry D Wilkins, III
*Assistant Examiner*—Bryan D. Ripa
(74) *Attorney, Agent, or Firm*—McGlew and Tuttle, P.C.

(57) ABSTRACT

A gas-measuring system contains at least one gas sensor (1) and at least one gas generator (4). The gas sensor (1) has at least one measuring surface (3), at which a target gas concentration can be measured. The gas generator (4) has at least one discharge surface (5), from which a current-proportional quantity of test gas can be discharged. The measuring surface (3) and the discharge surface (5) are designed and the gas sensor (1) and the gas generator (4) can be arranged such that the measuring surface (3) and the discharge surface (5) are in direct contact with the ambient atmosphere and the distance between the two surfaces is shorter than the extension of the smaller of the two surfaces.

2 Claims, 2 Drawing Sheets

GAS-MEASURING SYSTEM WITH GAS SENSOR AND GAS GENERATOR

CROSS REFERENCE TO RELATED APPLICATIONS

This application claims the benefit of priority under 35 U.S.C. § 119 of German Patent Application 10 2005 017 445.0 filed Apr. 15, 2005, the entire contents of which are incorporated herein by reference.

FIELD OF THE INVENTION

The present invention pertains to a gas-measuring system with a gas sensor and a gas generator. Such systems can be used advantageously wherever the readiness of gas-measuring systems to operate must be guaranteed over a rather long time. This applies, for example, to the use of permanently installed gas warning means or mobile gas-measuring systems that are in use for a rather long time.

BACKGROUND OF THE INVENTION

In case of the use of gas warning means, it is necessary essentially for two reasons to let the gas sensors used respond in a specific manner. First, an undiagnosed failure of a gas sensor, e.g., due to blockage of the entry of gas or inactivation of the detector element, may lead to safety-relevant risks in an area being monitored. The sensor must therefore be subjected to function tests at short intervals. Second, commercially available gas sensors have a drift in the sensitivity of the sensor with respect to the species to be detected. This behavior of the sensor cannot be described or predicted by mathematical formulas. It is therefore necessary to calibrate sensors within certain time intervals with a target gas of a known concentration. The duration of the time intervals is determined by the requirements imposed on the desired accuracy of the sensor. Guidelines for the handling of this problem were summarized, e.g., in the specification T021 of the Trade Association of the Chemical Industry.

The proper function of the sensor is tested best by admitting the target gas into the sensor. This is the only way the entire functional chain from the gas supply to the signal generation can be checked. It is therefore common practice to stock calibrating agents, e.g., in the form of gas cylinders, often with toxic gases, to transport these to the sensor, and finally to introduce the test gas into the gas inlet of the particular sensor through suitable devices, e.g., pumps, valves and/or mass flow controllers. The expense of carrying out these function tests and calibration procedures is high.

To avoid this expense, it is known that a gas generator can be accommodated together with a gas sensor in a common housing (GB 2,254,696). The common housing is limited toward the measured gas by a gas-permeable membrane. Occasional activation of the gas generator thus makes it possible to test the sensor function, but it fails to provide information on the state of the transport paths via which the target gas enters during regular measuring operation. These transport paths are determined, for example, by a gas-permeable membrane, through which the target gas can reach the detector electrode.

Furthermore, it is known that test gas can be sent through a membrane, which is also connected to a gas generator and a sensor, in a similar manner (EP 0,744,620 B1). It is difficult to infer the state of the outer membrane granting access for the gas to the detector electrode in this case as well.

Furthermore, it is known that test gas can be injected into a test gas chamber via detector electrodes in the interior of the sensor housing. The test gas chamber is arranged downstream of the outer gas inlet (U.S. Pat. No. 6,635,160). However, the entry of gas from the outside to this chamber and consequently also to the detector electrode of the sensor continues to be untested in this design as well.

Furthermore, diagnostic methods for sensors are known, with which test gas is pressed mechanically through an aperture to a sensor, delivered by adding a propellant or is moved to the sensor by thermal expansion (U.S. Pat. No. 4,151,739). These methods also have the drawback that the path of the ambient gases to the detector electrode is not tested under realistic conditions.

SUMMARY OF THE INVENTION

The object of the present invention is to provide a reliable testing and calibration that makes possible a complete function testing and/or calibration of gas sensors at a low cost.

A gas-measuring system according to the present invention comprises at least one gas sensor and a gas generator. The present invention can be embodied, in principle, with gas sensors and gas generators, the principle of operation of the elements used being less important than their geometric nature. A gas sensor is therefore defined in the sense of the present invention as any assembly unit that sends an evaluable signal in the presence of a detectable concentration of a target gas. A gas generator is defined in the sense of the present invention as any assembly unit that can deliver a defined quantity of this target gas. Typical gas sensors are electrochemical gas sensors.

The present invention comprises a gas-measuring system, which contains at least one gas sensor and at least one gas generator, the gas sensor having at least one measuring surface at which a target gas concentration can be measured, and a gas generator has at least one discharge surface, from which a quantity of test gas that is proportional to the current can be discharged, the measuring surface and the discharge surface being designed and the gas sensor and the gas generator being able to be arranged such that the measuring surface and the discharge surface are in direct contact with the ambient atmosphere and the distance between the two surfaces is shorter than the extension of the smaller of the two surfaces. The extension of the surface (also referred to as the extent) is defined, as a function of the shape of the surface, as a characteristic length, for example, the diameter or a side length, which can be used to describe the size of the surface. The distance between the measuring surface and the discharge surface is advantageously shorter than this characteristic length by one order of magnitude.

The present invention advantageously comprises a gas-measuring system, which contains at least one gas sensor and at least one gas generator, wherein the gas sensor has at least one measuring surface, at which a target gas concentration can be measured, and the gas generator has at least one discharge surface, from which a current-proportional quantity of test gas can be discharged, the measuring surface and the discharge surface being shaped and the gas sensor and the gas generator being able to be arranged such that the measuring surface and the discharge surface have a common axis of symmetry, the two surfaces are in direct contact with the ambient atmosphere, and the distance between the two surfaces is smaller than the shortest distance between the edge of one of the two surfaces and the axis of symmetry.

The measuring surface of the gas sensor can be formed, for example, by a usual gas-permeable membrane, through which a target gas enters the interior space of an electrochemical sensor. A change in the concentration of the target gas at this measuring surface can be quantified as a change in the initial signal of the gas sensor.

An essential advantage of the present invention is that the test gas does not have to be delivered actively to the sensor and the device has minimal fault susceptibility to environmental effects due to the proximity in space of the gas generator and the detector. The fact that the measuring surface and the discharge surface are arranged adjacent to one another makes it possible to admit very small quantities of target gas to the gas sensor. It was found that especially if the above-described advantageous symmetry condition is complied with, a configuration is obtained that is characterized by a surprisingly stable operation and even permits undisturbed and reliable operation under extreme external air flows.

The gas sensor and the gas generator may be designed according to the present invention as separate assembly units capable of operating independently from one another. The designs of the assembly units are of secondary importance. However, these units must be designed such that the closely spaced arrangement according to the present invention of the measuring surface of the gas generator and the discharge surface of the gas generator is possible for testing and calibration purposes. Arrangements in which the distance according to the present invention is maintained and there are no flow obstacles in the direct path between the measuring surface and the discharge surface are considered to be closely adjacent to one another. It proved to be especially advantageous if the two surfaces are exposed to the same flow conditions during testing and/or calibration. This is achieved, for example, by a radially symmetrical arrangement, in which the measuring surface and the discharge surface are located in one plane. The measuring surface may surround the discharge surface either radially symmetrically or vice versa.

The present invention will be explained on the basis of two exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
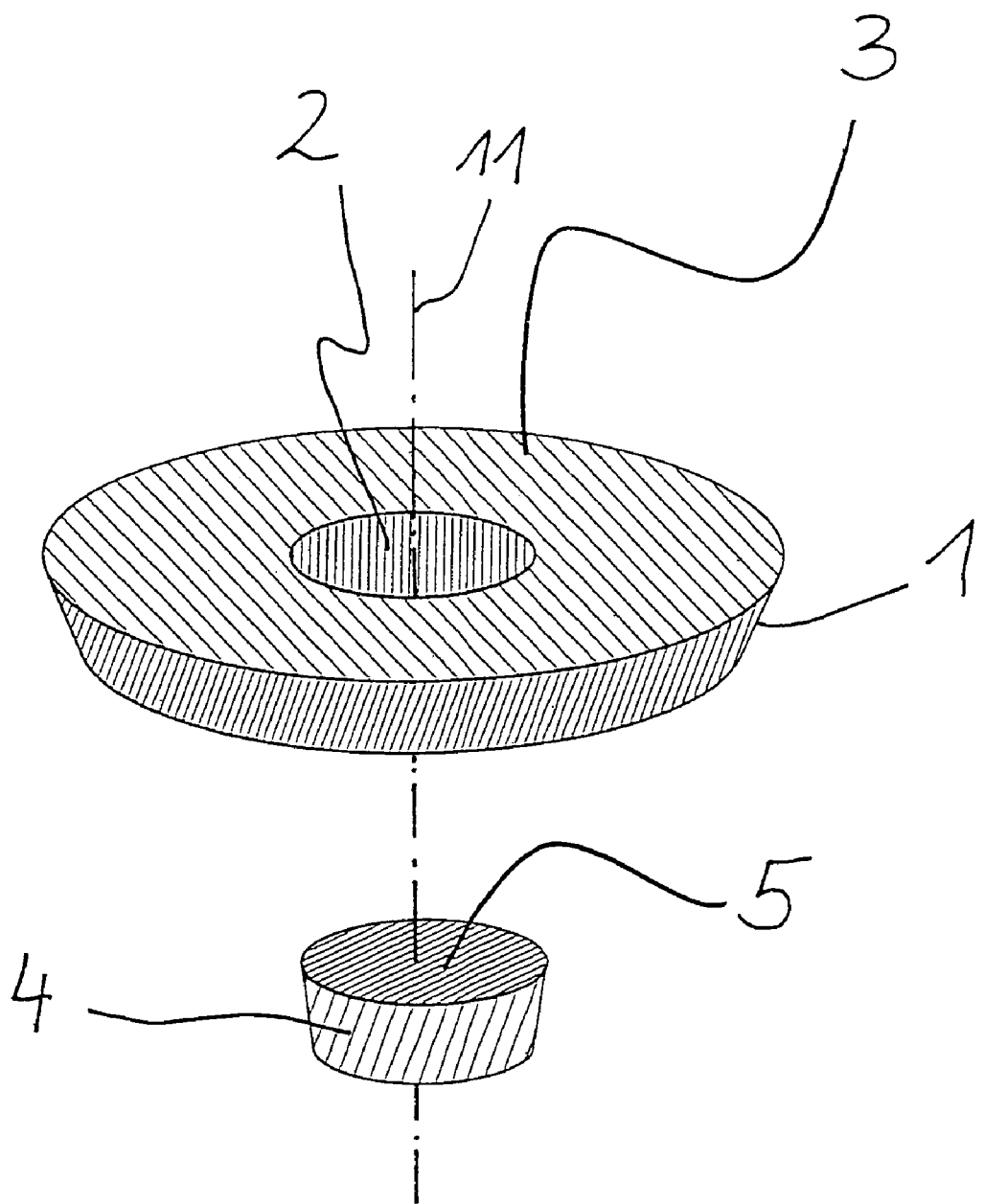
FIG. 1 is a schematic view showing a gas-measuring system according to the present invention, which can be arranged according to the lock-and-key principle.

Referring to the drawings in particular, FIG. 1 shows a gas-measuring system according to the present invention. It comprises as the gas sensor 1 an electrochemical three-electrode sensor, as it can be used to detect hydrogen sulfide. The sensor contains a working electrode consisting of iridium, an auxiliary electrode consisting of platinum, and a platinum/platinum oxide reference electrode. Sulfuric acid is used as the electrolyte. The housing of the sensor has the shape of a flat truncated cone and has an opening 2 in the center. The base is closed with a gas-permeable membrane and acts in the sense of the present invention as a measuring surface 3, at which a target gas concentration can be measured. The gas-measuring system according to the present invention comprises, furthermore, a tablet-shaped hydrogen sulfide generator as the gas generator. A base of the generator acts as a discharge surface 5 in the sense of the present invention, from which a quantity of hydrogen sulfide, which is proportional to the resulting current flow, is discharged when a voltage is applied.

The gas sensor and the gas generator are designed as completely separate assembly units. The diameter of the tablet-shaped hydrogen sulfide generator is selected to be such that it fits into the central opening 2 of the sensor. It is possible as a result that the gas sensor 1 and the gas generator 4 can be fitted into one another according to the lock-and-key principle, i.e., one assembly unit surrounds the other in a radially symmetrical manner in the testing and calibrating mode. At the same time, the measuring surface 3 and the discharge surface 5 are located in one plane when the gas sensor 1 and the gas generator 4 are fitted into one another.

Both assembly units are also able to function individually as sensor and gas generator, respectively, but they become a complete system capable of performing the analysis due to the above-described fitting together. In a geometric variant, both the sensor and the gas generator can assume the function of the key or the function of the lock. In the state in which they are fitted together, the gas sensor 1 and the gas generator 4 have a common axis of symmetry 11.

Figure 2:
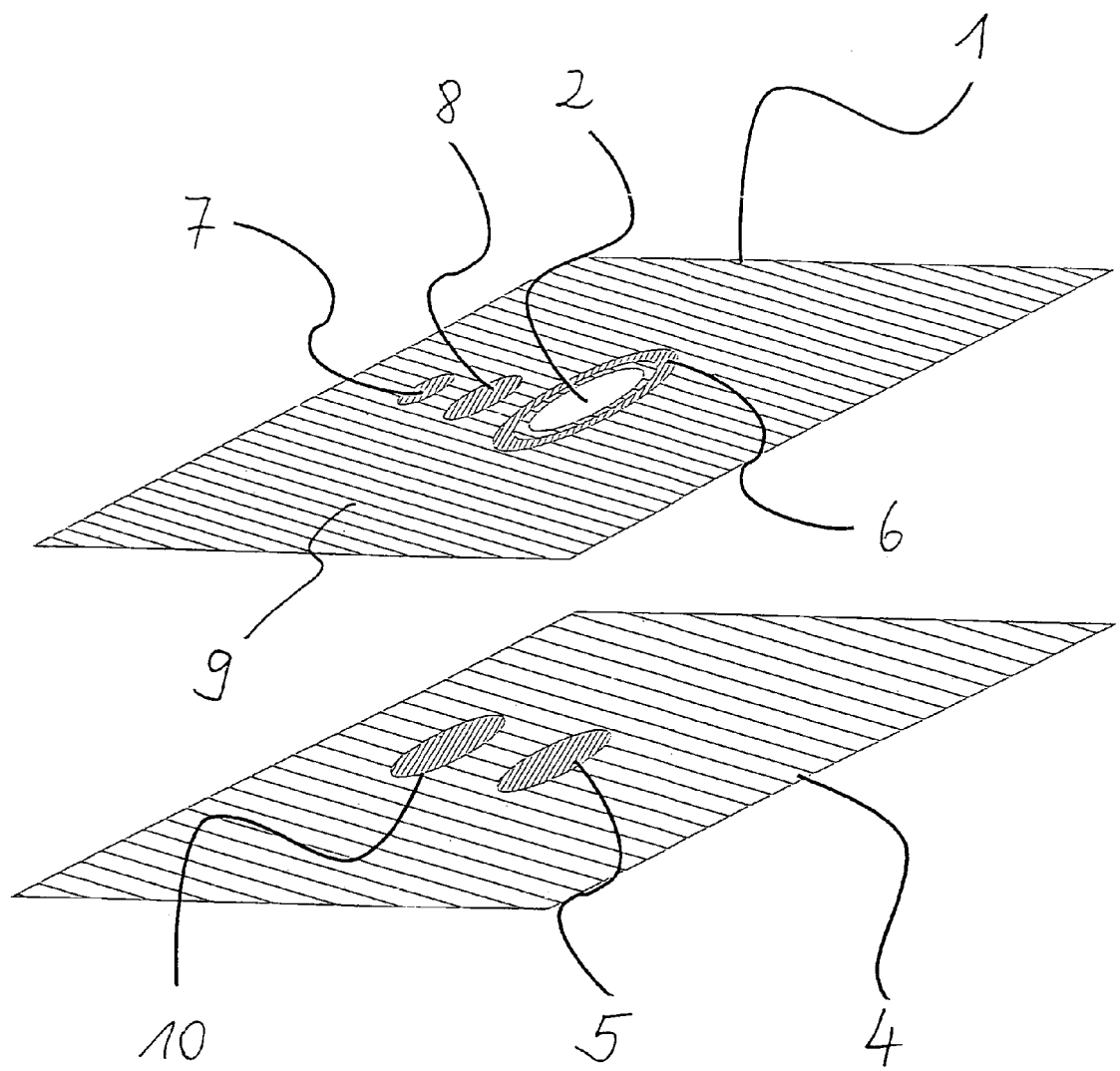
FIG. 2 is a schematic view showing a gas-measuring system according to the present invention, which comprises a gas sensor and a gas generator in the form of planar assembly units, which can be brought flatly into contact with one another.

FIG. 2 shows a gas-measuring system according to the present invention, which comprises a gas sensor 1 and a gas generator 4 in the form of planar assembly units, which can be brought flat into contact with one another. The gas sensor 1 and the gas generator 4 are again designed as completely separate, planar assembly units. The gas sensor 1 is likewise designed as a three-electrode sensor and contains the same electrode and electrolyte materials as the sensor according to FIG. 1. The working electrode 6 has a ring-shaped design and is arranged in one plane with the auxiliary electrode 7 and the reference electrode 8. The electrodes are located in a flat electrolyte reservoir, which is surrounded by a flexible housing 9. It is ensured on the part of the measuring gas that the measuring gas can reach the ring-shaped working electrode 6. This can be embodied, for example, by a gas-permeable membrane, which makes it possible for the measuring gas to gain access to the working electrode 6. The ring-shaped working electrode 6 surrounds a circular opening 2, which passes through the sensor housing. The gas generator 4 with a disk-shaped generator electrode 10 and a gas outlet membrane acting as a discharge surface 5 can be placed during operation such that the discharge surface 5, from which the test gas is discharged, will completely fill the circular opening 2 in the center of the ring-shaped working electrode 6 of the gas sensor 1 without, however, being covered.

The particular assembly unit in which an opening is arranged is likewise unimportant in this embodiment. The thing that is important is that one of the two assembly units has an opening (hole), which is shaped such that the element of the other assembly unit, which element performs the function, shall fit into this opening as accurately as possible. The two assembly units can then be brought to close proximity in space due to an arrangement in which the assembly unit with the opening is arranged in front of the assembly unit without an opening, and thus they permit the detector element to be accommodated in the "sphere of influence" of the test gas generator.

While specific embodiments of the invention have been shown and described in detail to illustrate the application of the principles of the invention, it will be understood that the invention may be embodied otherwise without departing from such principles.

What is claimed is:

1. A gas-measuring system comprising:
a gas sensor with a measuring surface, with an ambient atmosphere side, at which a target gas concentration, at the atmosphere side, is measured, said measuring surface having a maximum measuring surface dimension of an area of said measuring surface;
a gas generator with a discharge surface, with an ambient atmosphere side, for discharging a quantity of test gas to the atmosphere side, said discharge surface having a maximum discharge surface dimension of an area of said discharge surface, said measuring surface and said discharge surface being in direct contact with ambient atmosphere, at the atmosphere side, with a distance between said measuring surface and said discharge surface being smaller than each of said maximum measuring surface dimension and said maximum discharge surface dimension, wherein:
said gas sensor and said gas generator each a form planar assembly unit, with the units brought flatly into contact with one another; and
said measuring surface is arranged ring-shaped, around an opening in said gas sensor and said discharge surface is arranged behind said opening with said gas sensor and said gas generator brought into flat contact with one another.

2. A gas-measuring system comprising:
a gas sensor with a measuring surface, with an ambient atmosphere side, at which a target gas concentration, at the atmosphere side, is measured, said measuring surface having a maximum measuring surface dimension of an area of said measuring surface;
a gas generator with a discharge surface, with an ambient atmosphere side, for discharging a quantity of test gas to the atmosphere side, said discharge surface having a maximum discharge surface dimension of an area of said discharge surface, said measuring surface and said discharge surface being in direct contact with ambient atmosphere, at the atmosphere side, with a distance between said measuring surface and said discharge surface being smaller than each of said maximum measuring surface dimension and said maximum discharge surface dimension, wherein:
said gas sensor and said gas generator each forming a planar assembly unit with the units brought flatly into contact with one another; and
said discharge surface is arranged around an opening in said gas generator in a ring-shaped manner and said measuring surface is arranged behind said opening with said gas sensor and said gas generator brought into flat contact with one another.

* * * * *